United States Patent
De Paul et al.

(10) Patent No.: US 8,735,408 B2
(45) Date of Patent: May 27, 2014

(54) SOLID FORMS OF 3-(4-(AMINOMETHYL)-1-(5-METHYL-7H-PYRROLO[2,3-D]PYRIMIDIN-4-YL) PIPERIDINE-4-CARBOXAMIDO)PHENYL DIMETHYLCARBAMATE

(75) Inventors: Susan Margaret De Paul, Zürich (CH); Qun Li, Newark, DE (US); Haiming Zhang, San Mateo, CA (US)

(73) Assignee: Lexicon Pharmaceuticals, Inc., The Woodlands, TX (US)

( * ) Notice: Subject to any disclaimer, the term of this patent is extended or adjusted under 35 U.S.C. 154(b) by 170 days.

(21) Appl. No.: 13/288,321

(22) Filed: Nov. 3, 2011

(65) Prior Publication Data

US 2012/0122898 A1 May 17, 2012

Related U.S. Application Data

(60) Provisional application No. 61/410,602, filed on Nov. 5, 2010.

(51) Int. Cl.
*C07D 487/04* (2006.01)
*A61K 31/519* (2006.01)
*A61P 27/06* (2006.01)

(52) U.S. Cl.
USPC .......................... 514/265.1; 544/280

(58) Field of Classification Search
USPC .......................... 544/280; 514/265.1
See application file for complete search history.

(56) References Cited

U.S. PATENT DOCUMENTS 8,193,202 B2  6/2012  Burgoon et al.
8,450,332 B2  5/2013  Burgoon

OTHER PUBLICATIONS

Anderson, *Practical Process Res. Dev.* 223-247 (2000).
Bastin et al, *Org. Process Res. Dev.* 4(5):427-435 (2000).
Caira, *Topics in Current Chemistry* 198:163-208 (1998).
International Search Report issued in corresponding international application No. PCT/US2011/059086, dated Feb. 21, 2012.

*Primary Examiner* — Susanna Moore
(74) *Attorney, Agent, or Firm* — Max Bachrach

(57) ABSTRACT

Solid forms of 3-(4-(aminomethyl)-1-(5-methyl-7H-pyrrolo [2,3-d]pyrimidin-4-yl)piperidine-4-carboxamido)phenyl dimethylcarbamate and salts thereof are disclosed. Methods of its use to treat diseases and disorders of the eye are also disclosed.

17 Claims, 3 Drawing Sheets

US 8,735,408 B2

SOLID FORMS OF 3-(4-(AMINOMETHYL)-1-(5-METHYL-7H-PYRROLO[2,3-D]PYRIMIDIN-4-YL)PIPERIDINE-4-CARBOXAMIDO)PHENYL DIMETHYLCARBAMATE

This application claims priority to U.S. provisional patent application No. 61/410,602, filed Nov. 5, 2011, the entirety of which is incorporated herein by reference.

1. FIELD OF THE INVENTION

This invention relates to solid forms of 3-(4-(aminomethyl)-1-(5-methyl-7H-pyrrolo[2,3-d]pyrimidin-4-yl)piperidine-4-carboxamido)phenyl dimethylcarbamate and salts thereof, compositions comprising them, and methods of their use.

2. BACKGROUND OF THE INVENTION

Different solid forms of the same compound can have substantially different properties. For example, the amorphous form of a drug may exhibit different dissolution characteristics and different bioavailability patterns than its crystalline form(s), properties which can affect how the drug must be administered to achieve optimal effect. Amorphous and crystalline forms of a drug may also have different handling properties (e.g., flowability, compressibility), dissolution rates, solubilities and stabilities, all of which can affect the manufacture of dosage forms. Consequently, access to multiple forms of a drug is desirable for a variety of reasons. Moreover, regulatory authorities (e.g., the U.S. Food and Drug Administration) may require the identification of all solid forms of a new drug substance before approving products containing it. A. Goho, *Science News* 166(8):122-123 (2004).

Compounds may exist in one or more crystalline forms, but the existence and characteristics of those forms cannot be predicted with any certainty. And even after one polymorph has been identified, the existence and characteristics of other forms can only be determined by additional experimentation. Id.

3. SUMMARY OF THE INVENTION

This invention is directed, in part, to solid forms of the LIM kinase 2 inhibitor 3-(4-(aminomethyl)-1-(5-methyl-7H-pyrrolo[2,3-d]pyrimidin-4-yl)piperidine-4-carboxamido)phenyl dimethylcarbamate and pharmaceutically acceptable salts thereof. Particular solid forms are crystalline.

One embodiment of the invention encompasses pharmaceutical compositions comprising the solid forms described herein. Another encompasses methods of treating, managing, and/or preventing diseases or disorders affecting vision in a patient (e.g., glaucoma), which comprises administering to a patient a solid form of the invention.

4. BRIEF DESCRIPTION OF THE FIGURES

Certain aspects of the invention may be understood with reference to the attached figures.

Figure 1:
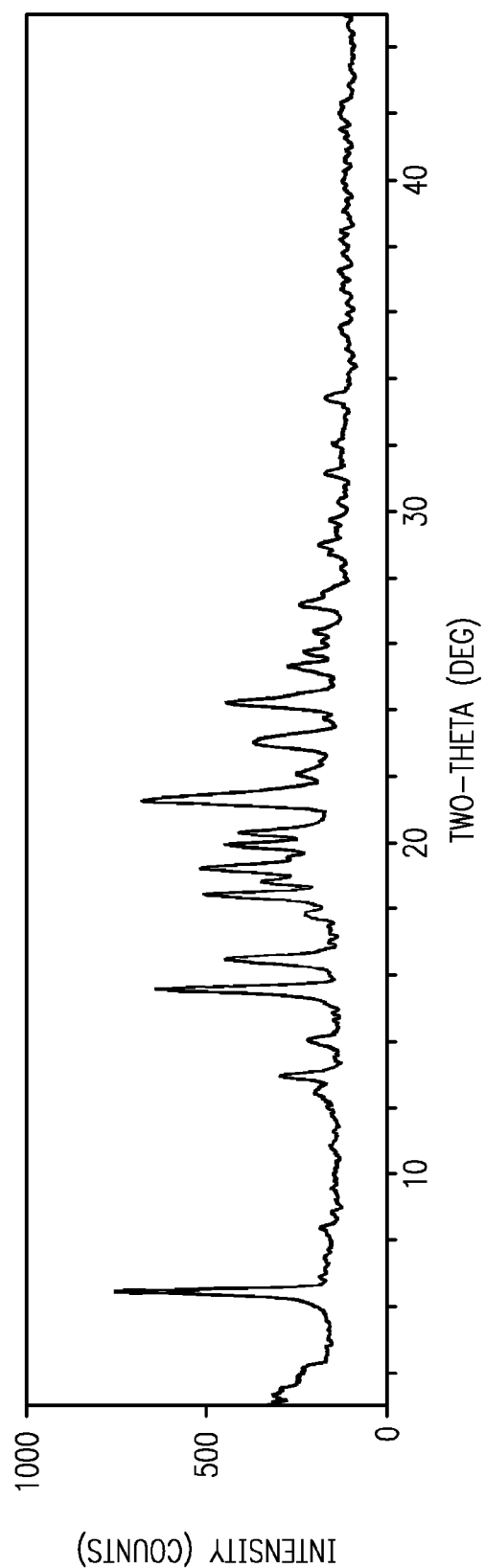

FIG. 1 is an X-ray diffraction (XRPD) pattern of crystalline 1-(5-methyl-7H-pyrrolo[2,3-d]pyrimidin-4-yl)piperidine-4-carboxamido)phenyl dimethylcarbamate benzoate. The spectrum was obtained using a Rigaku MiniFlex instrument: Cu radiation (1.054056 Å) with $K_\beta$ filter: 3 degree start angle; 45 degree stop angle, 0.02 degree sampling; 2 degree/minute scan speed. The sample material was dispersed on a zero-background sample holder.

Figure 2:
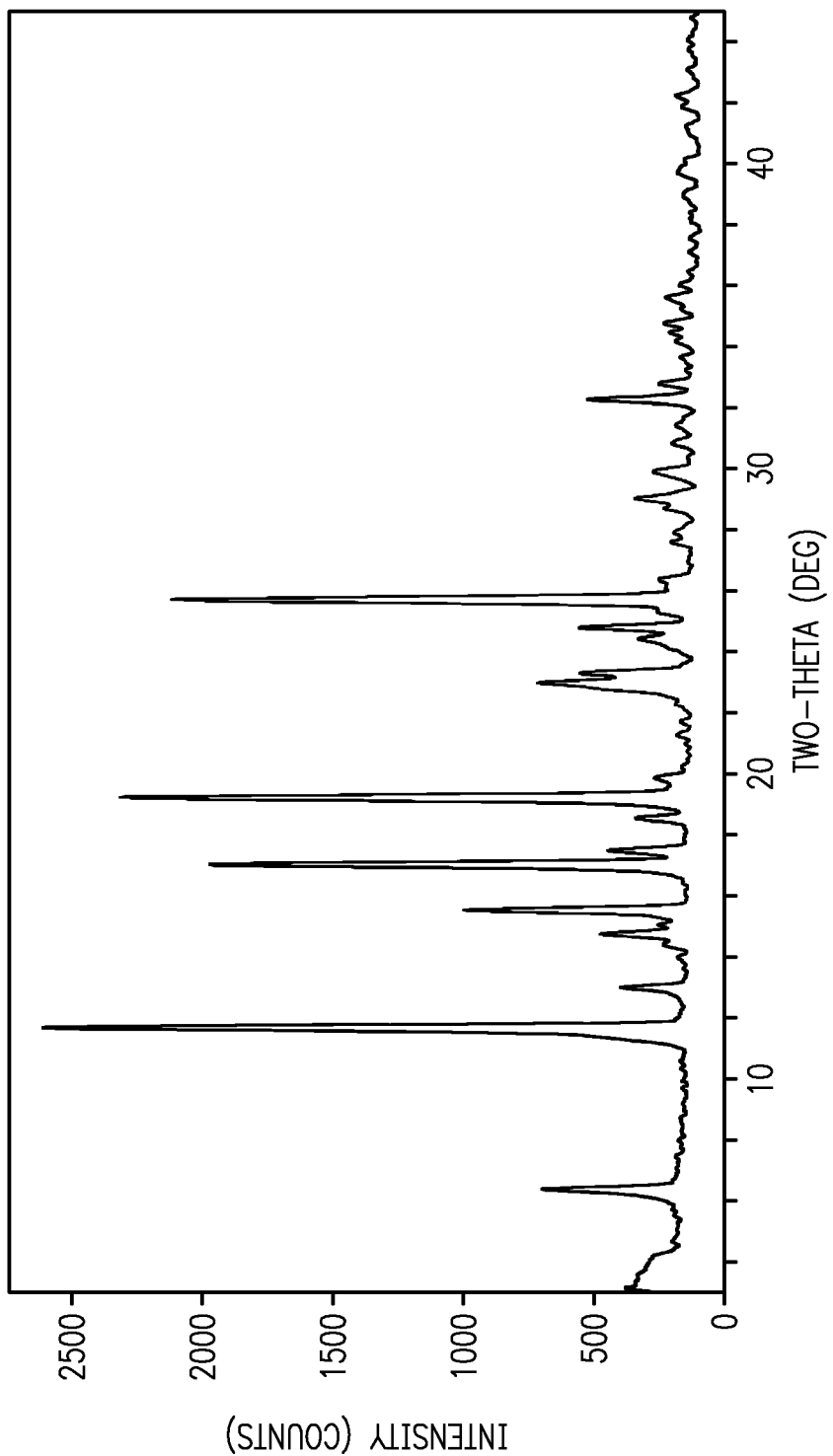

FIG. 2 is an X-ray diffraction (XRPD) pattern of crystalline 1-(5-methyl-7H-pyrrolo[2,3-d]pyrimidin-4-yl)piperidine-4-carboxamido)phenyl dimethylcarbamate hydrochloride. The spectrum was obtained using a Rigaku MiniFlex instrument: Cu radiation (1.054056 Å) with $K_\beta$ filter: 3 degree start angle; 45 degree stop angle, 0.02 degree sampling; 2 degree/minute scan speed. The sample material was dispersed on a zero-background sample holder.

Figure 3:
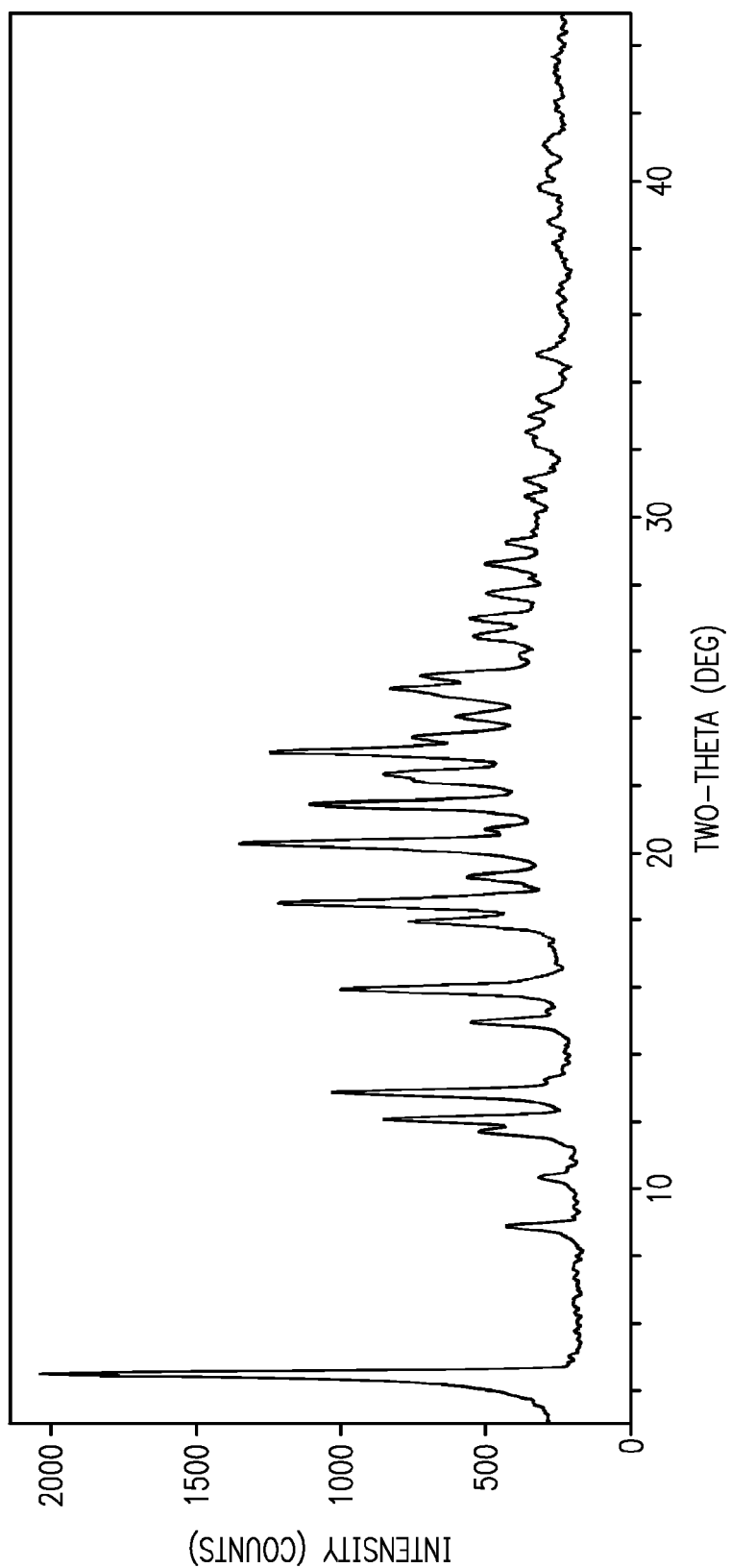

FIG. 3 is an X-ray diffraction (XRPD) pattern of crystalline 1-(5-methyl-7H-pyrrolo[2,3-d]pyrimidin-4-yl)piperidine-4-carboxamido)phenyl dimethylcarbamate phosphate. The spectrum was obtained using a Rigaku MiniFlex instrument: Cu radiation (1.054056 Å) with $K_\beta$ filter: 3 degree start angle; 45 degree stop angle, 0.02 degree sampling; 2 degree/minute scan speed. The sample material was dispersed on a zero-background sample holder.

5. DETAILED DESCRIPTION OF THE INVENTION

This invention is directed, in part, to solid (e.g., crystalline) forms of 3-(4-(aminomethyl)-1-(5-methyl-7H-pyrrolo[2,3-d]pyrimidin-4-yl)piperidine-4-carboxamido)phenyl dimethylcarbamate, and pharmaceutically acceptable salts thereof. The compound, which is an inhibitor of LIM kinase 2, and has been shown to decrease intraocular pressure in models of ophthalmic disease, and may be useful in the treatment, management, or prevention of glaucoma. See U.S. patent application publication US-2009-0264450-A1.

This invention is also directed to pharmaceutical compositions comprising solid forms of 3-(4-(aminomethyl)-1-(5-methyl-7H-pyrrolo[2,3-d]pyrimidin-4-yl)piperidine-4-carboxamido)phenyl dimethylcarbamate, and to methods of their use.

5.1. DEFINITIONS

Unless otherwise indicated, the terms "manage," "managing" and "management" encompass preventing the recurrence of the specified disease or disorder in a patient who has already suffered from the disease or disorder, and/or lengthening the time that a patient who has suffered from the disease or disorder remains in remission. The terms encompass modulating the threshold, development and/or duration of the disease or disorder, or changing the way that a patient responds to the disease or disorder.

Unless otherwise indicated, the terms "prevent," "preventing" and "prevention" contemplate an action that occurs before a patient begins to suffer from the specified disease or disorder, which inhibits or reduces the severity of the disease or disorder. In other words, the terms encompass prophylaxis.

Unless otherwise indicated, a "prophylactically effective amount" of a compound is an amount sufficient to prevent a disease or condition, or one or more symptoms associated with the disease or condition, or to prevent its recurrence. A prophylactically effective amount of a compound means an amount of therapeutic agent, alone or in combination with other agents, which provides a prophylactic benefit in the prevention of the disease or condition. The term "prophylactically effective amount" can encompass an amount that improves overall prophylaxis or enhances the prophylactic efficacy of another prophylactic agent.

Unless otherwise indicated, a "therapeutically effective amount" of a compound is an amount sufficient to provide a therapeutic benefit in the treatment or management of a disease or condition, or to delay or minimize one or more symptoms associated with the disease or condition. A therapeutically effective amount of a compound means an amount of therapeutic agent, alone or in combination with other therapies, which provides a therapeutic benefit in the treatment or management of the disease or condition. The term "therapeutically effective amount" can encompass an amount that improves overall therapy, reduces or avoids symptoms or causes of a disease or condition, or enhances the therapeutic efficacy of another therapeutic agent.

Unless otherwise indicated, the terms "treat," "treating" and "treatment" contemplate an action that occurs while a patient is suffering from the specified disease or disorder, which reduces the severity of the disease or disorder or one or more of its symptoms, or retards or slows the progression of the disease or disorder.

Unless otherwise indicated, the term "include" has the same meaning as "include, but are not limited to," and the term "includes" has the same meaning as "includes, but is not limited to." Similarly, the term "such as" has the same meaning as the term "such as, but not limited to."

5.2. SOLID FORMS

This invention is directed to solid forms of 3-(4-(aminomethyl)-1-(5-methyl-7H-pyrrolo[2,3-d]pyrimidin-4-yl)piperidine-4-carboxamido)phenyl dimethylcarbamate:

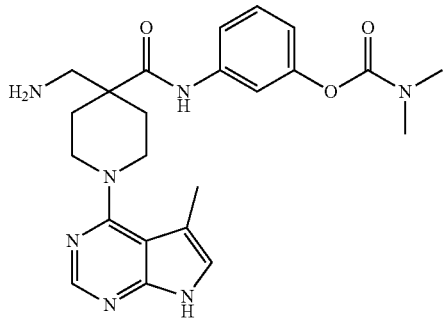 [SMILES: Cc1c[nH]c2ncnc(N3CCC(CN)(C(=O)Nc4cccc(OC(=O)N(C)C)c4)CC3)c12]

and salts thereof. Particular solid forms are crystalline. Specific salts include acetate, adipate, benzoate, besylate, fumarate, hydrochloride, maleate, nicotinate, and phosphate.

One embodiment of the invention encompasses crystalline 3-(4-(aminomethyl)-1-(5-methyl-7H-pyrrolo[2,3-d]pyrimidin-4-yl)piperidine-4-carboxamido)phenyl dimethylcarbamate. A particular form of this crystalline freebase has a differential scanning calorimeter (DSC) peak at about 177.9° C. In the context of DSC data (onsets and peaks), the term "about" as used herein means±3.5° C.

Another embodiment of the invention encompasses crystalline 3-(4-(aminomethyl)-1-(5-methyl-7H-pyrrolo[2,3-d]pyrimidin-4-yl)piperidine-4-carboxamido)phenyl dimethylcarbamate acetate. A particular form provides an X-ray diffraction (XRPD) pattern containing peaks at one or more of about 5.9, 9.1, 12.0, 16.1, 17.2, 18.4, and/or 20.2 degrees 2θ. Thus, one embodiment of the invention encompasses a crystalline acetate salt with an XRPD pattern having peaks at 5.9, 9.1, and 12.0 degrees 2θ. Another encompasses a crystalline acetate salt with an XRPD pattern having peaks at 12.0, 16.1, and 17.2 degrees 2θ. Another encompasses a crystalline acetate salt with an XRPD pattern having peaks at 12.0, 16.1, and 17.2 degrees 2θ. 17.2, 18.4, and 20.2 degrees 2θ. In the context of XRPD data, the term "about" as used herein means±0.3 degrees 2θ.

Another embodiment of the invention encompasses crystalline 3-(4-(aminomethyl)-1-(5-methyl-7H-pyrrolo[2,3-d]pyrimidin-4-yl)piperidine-4-carboxamido)phenyl dimethylcarbamate adipate. A particular form provides an XRPD pattern containing peaks at one or more of about 5.6, 21.5, and/or 22.5 degrees 2θ.

Another embodiment of the invention encompasses crystalline 3-(4-(aminomethyl)-1-(5-methyl-7H-pyrrolo[2,3-d]pyrimidin-4-yl)piperidine-4-carboxamido)phenyl dimethylcarbamate benzoate. A particular form has a melting point of about 192.3° C. as determined by DSC (onset temperature). A particular form has a DSC peak at about 194.5° C. A particular form provides an XRPD pattern containing peaks at one or more of about 6.5, 15.6, 16.5, 18.4, 19.2, 21.3, and/or 24.2 degrees 2θ. Thus, one embodiment of the invention encompasses a crystalline benzoate salt with an XRPD pattern having peaks at 6.5, 15.6, and 16.5 degrees 2θ. Another encompasses a crystalline benzoate salt with an XRPD pattern having peaks at 16.5, 18.4, and 19.2 degrees 2θ. As those skilled in the art are well aware, the relative intensities of peaks in a XRPD pattern of a crystalline material can vary depending on how the sample is prepared and how the data is collected. With this in mind, an example of a XRPD pattern of this crystalline form is provided in FIG. 1.

Another embodiment of the invention encompasses crystalline 3-(4-(aminomethyl)-1-(5-methyl-7H-pyrrolo[2,3-d]pyrimidin-4-yl)piperidine-4-carboxamido)phenyl dimethylcarbamate besylate. A particular form provides an XRPD pattern containing peaks at one or more of about 5.6, 9.8, 15.0, 17.0, 19.6, 20.4, 22.7, and/or 24.8 degrees 2θ. Thus, one embodiment of the invention encompasses a crystalline besylate salt with an XRPD pattern having peaks at 5.6, 9.8, and 15.0 degrees 2θ. Another encompasses a crystalline besylate salt with an XRPD pattern having peaks at 15.0, 17.0, and 19.6 degrees 2θ. Another encompasses a crystalline besylate salt with an XRPD pattern having peaks at 20.4, 22.7, and 24.8 degrees 2θ.

Another embodiment of the invention encompasses crystalline 3-(4-(aminomethyl)-1-(5-methyl-7H-pyrrolo[2,3-d]pyrimidin-4-yl)piperidine-4-carboxamido)phenyl dimethylcarbamate fumarate. A particular form provides an XRPD pattern containing peaks at one or more of about 6.4, 10.5, 15.6, 20.5, and/or 25.4 degrees 2θ. Thus, one embodiment of the invention encompasses a crystalline fumarate salt with an XRPD pattern having peaks at 6.4, 10.5, and 15.6 degrees 2θ.

Another embodiment of the invention encompasses crystalline 3-(4-(aminomethyl)-1-(5-methyl-7H-pyrrolo[2,3-d]pyrimidin-4-yl)piperidine-4-carboxamido)phenyl dimethylcarbamate hydrochloride. A particular form is anhydrous. A particular form has a melting point of about 245.8° C. as determined by DSC (onset temperature). A particular form has a DSC peak at about 248.9° C. A particular form provides an XRPD pattern containing peaks at one or more of about 6.4, 11.7, 17.0, 19.2, 23.0, and/or 25.7 degrees 2θ. Thus, one embodiment of the invention encompasses a crystalline hydrochloride salt with an XRPD pattern having peaks at 6.4, 11.7, and 17.0 degrees 2θ. Another encompasses a crystalline hydrochloride salt with an XRPD pattern having peaks at 17.0, 19.2, and 23.0 degrees 2θ. Another encompasses a crystalline hydrochloride salt with an XRPD pattern having peaks at 23.0 and 25.7 degrees 2θ. An example of a XRPD pattern of crystalline 3-(4-(aminomethyl)-1-(5-methyl-7H-pyrrolo[2,3-d]pyrimidin-4-yl)piperidine-4-carboxamido)phenyl dimethylcarbamate hydrochloride is provided in FIG. 2.

Another embodiment of the invention encompasses crystalline 3-(4-(aminomethyl)-1-(5-methyl-7H-pyrrolo[2,3-d]pyrimidin-4-yl)piperidine-4-carboxamido)phenyl dimethylcarbamate maleate. A particular form provides an XRPD pattern containing peaks at one or more of about 7.9, 15.9, 20.2, 24.0, 26.1, and/or 32.2 degrees 2θ. Thus, one embodiment of the invention encompasses a crystalline maleate salt with an XRPD pattern having peaks at 7.9, 15.9, and 20.2 degrees 2θ. Another encompasses a crystalline maleate salt with an XRPD pattern having peaks at 24.0, 26.1, and 32.2 degrees 2θ.

Another embodiment of the invention encompasses crystalline 3-(4-(aminomethyl)-1-(5-methyl-7H-pyrrolo[2,3-d]pyrimidin-4-yl)piperidine-4-carboxamido)phenyl dimethylcarbamate nicotinate. A particular form provides an XRPD pattern containing peaks at one or more of about 8.3, 18.4, 25.1, 26.4, and/or 29.6 degrees 2θ. Thus, one embodiment of the invention encompasses a crystalline nicotinate salt with an XRPD pattern having peaks at 8.3, 18.4, and 25.1 degrees 2θ.

Another embodiment of the invention encompasses crystalline 3-(4-(aminomethyl)-1-(5-methyl-7H-pyrrolo[2,3-d]pyrimidin-4-yl)piperidine-4-carboxamido)phenyl dimethylcarbamate phosphate. A particular form is a monohydrate. A particular form has a melting point of about 164.6° C. as determined by DSC (onset temperature). A particular form has a DSC peak at about 170.9° C. A particular form provides an XRPD pattern containing peaks at one or more of about 4.5, 12.9, 16.0, 18.5, 20.3, 21.4, and/or 23.0 degrees 2θ. An example of a XRPD pattern of this crystalline form is provided in FIG. 3. Thus, one embodiment of the invention encompasses a crystalline phosphate salt with an XRPD pattern having peaks at 4.5, 12.9, and 16.0 degrees 2θ. Another encompasses a crystalline phosphate salt with an XRPD pattern having peaks at 16.0, 18.5, and 20.3 degrees 2θ. Another encompasses a crystalline phosphate salt with an XRPD pattern having peaks at 20.3, 21.4, and 23.0 degrees 2θ.

This invention encompasses solids that are mixtures of both amorphous and crystalline forms. Certain such solids comprise crystalline 3-(4-(aminomethyl)-1-(5-methyl-7H-pyrrolo[2,3-d]pyrimidin-4-yl)piperidine-4-carboxamido)phenyl dimethylcarbamate or a pharmaceutically salt thereof in an amount of at least about 50, 75, 80, 85, 90, 95 or 99 weight percent.

Crystalline forms of 3-(4-(aminomethyl)-1-(5-methyl-7H-pyrrolo[2,3-d]pyrimidin-4-yl)piperidine-4-carboxamido)phenyl dimethylcarbamate can be prepared from the amorphous freebase, the synthesis of which is described in U.S. patent application publication no. US-2009-0264450-A1. In general, crystalline salts can be obtained by selecting a solvent in which the freebase is soluble, adding to it the appropriate acid of the desired salt, and stirring and heating the mixture. Evaporation, cooling, and/or the addition of an antisolvent to the mixture can afford the desired salt, which can be collected by filtration.

5.3. METHODS OF TREATMENT

This invention encompasses a method of lowering intraocular pressure in a patient, which comprises administering to a patient in need thereof a therapeutically or prophylactically effective amount of a compound of the invention.

Another embodiment encompasses a method of treating, managing or preventing a disease or disorder affecting vision in a patient, which comprises contacting the eye of the patient with a compound of the invention. Diseases and disorders affecting vision include glaucoma, neurodegenerative diseases, and infectious diseases.

5.4. PHARMACEUTICAL COMPOSITIONS

Compounds of the invention can be delivered to the eye (e.g., topically) using aqueous solutions, aqueous suspensions, and ointments. As those skilled in the art are aware, the ophthalmic product must be sterile in its final container to prevent microbial contamination of the eye. Preservatives may be used to maintain sterility once the container has been opened. Ophthalmic formulations also require that the pH, buffer capacity, viscosity, and tonicity of the formulation be controlled. Preferred formulations have a pH of from about 6.5 to 8.5, and a buffer capacity of from about 0.01 to 0.1. Particular formations are isotonic. Particular formations have a viscosity of from about 25 to 50 cps.

Ingredients that may be used to provide safe vehicles that effectively deliver an active pharmaceutical ingredient (API) to its site of action are well known, but will vary depending on the physical and chemical characteristics of the API.

Appropriately buffered aqueous solutions may be used for the delivery of water soluble compounds. In solution compositions, polymeric ingredients are typically used to increase the composition's viscosity. Examples of suitable polymers include cellulosic polymers (e.g., hydroxypropyl methylcellulose, hydroxyethyl cellulose, ethylhydroxyethyl cellulose), synthetic polymers (e.g., carboxyvinyl polymers, polyvinyl alcohol), polysaccharides (e.g., xanthan gum, guar gum, and dextran), and mixtures thereof. See, e.g., U.S. Pat. Nos. 4,136,173 and 7,244,440. Suspensions may also be used to deliver compounds. Polymeric ingredients are typically used in suspension compositions as physical stability aids, helping to keep the insoluble ingredients suspended or easily redispersible. Id.

Preservatives may be used to ensure the sterility of formations. Suitable preservatives include benzalkonium chloride, benzethonium chloride, chlorobutanol, phenylmercuric acetate, phenylmercuric nitrate, thimerosal, methylparaben, and propyl-parabens. And antioxidants may be used to ensure the stability of formations susceptible to oxidation. Suitable antioxidants include ethylenediaminetetraacetic acid, sodium bisulfite, sodium metabisulfite, and thiourea.

Particular pharmaceutical compositions of the invention comprise a solid form of 3-(4-(aminomethyl)-1-(5-methyl-7H-pyrrolo[2,3-d]pyrimidin-4-yl)piperidine-4-carboxamido)phenyl dimethylcarbamate, and are suitable for combining with one or more liquid vehicles to afford a final composition that is suitable for topical administration to the eye.

6. EXAMPLES

6.1. Preparation of Crystalline Benzoate Salt

Procedure A.

To a flask was added 3-(4-(aminomethyl)-1-(5-methyl-7H-pyrrolo[2,3-d]pyrimidin-4-yl)piperidine-4-carboxamido)phenyl dimethylcarbamate freebase (99.9 mg, 0.221 mmol, 1 eq) and acetonitrile (2.3 mL), followed by the addition of benzoic acid (33.1 mg, 0.271 mmol, 1.23 equiv). After the reaction mixture was stirred at room temperature for 30 minutes, methanol (0.5 mL) was added. The slurry was heated to 65° C. and stirred for 30 minutes, then methanol was evaporated. The reaction mixture was cooled to room temperature and stirred for 2 hours. The solid was collected by filtration, washed with MTBE (1 mL) and dried at 40-45° C. under vacuum overnight to afford 3-(4-(aminomethyl)-1-(5-methyl-7H-pyrrolo[2,3-d]pyrimidin-4-yl)piperidine-4-carboxamido)phenyl dimethylcarbamate benzoate (104.1 mg, 82.1%) as an off-white solid.

Procedure B.

A reactor was charged with 3-(4-(aminomethyl)-1-(5-methyl-7H-pyrrolo[2,3-d]pyrimidin-4-yl)piperidine-4-carboxamido)phenyl dimethylcarbamate freebase (101.1 mg, 0.224 mmol, 1 eq) and MeOH (1 mL). To the clear solution was added benzoic acid (33.9 mg, 0.278 mmol, 1.24 eq) and the resulting mixture was stirred at room temperature for 5 min to give a slurry. Acetonitrile (2 mL) was added and the slurry was heated to 70-73° C. and stirred for 5 minutes to give a solution. After being cooled to room temperature, the reaction mixture was stirred for 2 hours. The precipitate was collected by filtration and the cake was washed with MTBE (1 mL) and dried at 40-45° C. under vacuum overnight to provide the 3-(4-(aminomethyl)-1-(5-methyl-7H-pyrrolo[2,3-d]pyrimidin-4-yl)piperidine-4-carboxamido)phenyl dimethylcarbamate benzoate (94.8 mg, 75%) as an off-white solid

6.2. Preparation of Crystalline Phosphate Salt

A flask was charged 3-(4-(aminomethyl)-1-(5-methyl-7H-pyrrolo[2,3-d]pyrimidin-4-yl)piperidine-4-carboxamido) phenyl dimethylcarbamate freebase (101.1 mg, 0.224 mmol, 1 eq) and methanol (2.3 mL). To the solution was added dropwise phosphoric acid in IPA (0.246 mL 1 M, 0.246 mmol, 1.1 eq). The reaction mixture was stirred at room temperature for 10 minutes to give a sticky precipitate, heated with stirring at 65° C. for 1 hour, and then cooled to room temperature and stirred for 2 hours. The precipitated solids were collected by filtration. The cake was washed with MTBE (1 mL) and dried at 45° C. under vacuum overnight to provide the phosphate salt (103.7 mg, 85.4%) as an off-white solid.

6.3. Preparation of Crystalline Hydrochloride Salt 3-(4-((((Benzyloxy)carbonyl)amino)methyl)-1-(5-methyl-7H-pyrrolo[2,3-d]pyrimidin-4-yl)piperidine-4-carboxamido)phenyl dimethylcarbamate To a nitrogen inerted, 300-L stainless steel reactor at 20° C. were charged 53 kg of methanol and 4.5 kg (26.8 mol, 1.1 eq.) of 4-chloro-5-methyl-7H-pyrrolo[2,3-d]pyrimidine. The mixture was stirred for 10-30 minutes at 13° C., then added 12.0 kg of LP-911510 (24.4 mol, 1.0 eq.), stirred for another 10-30 minutes at 13° C. and then added 9.6 kg of N,N-diisopropylethylamine (74.3 mol, 3.0 eq.). The reaction mixture was then heated to 80-90° C. for 20-22 hours. After cooled to 30-35° C., the mixture was transferred to a 500-L glass lined reactor, followed by an isopropanol (40 kg) rinse. Additional 57 kg isopropanol was added into the mixture before 0.0116 kg of 3-(4-((((benzyloxy)carbonyl)amino)methyl)-1-(5-methyl-7H-pyrrolo[2,3-d]pyrimidin-4-yl(piperidine-4-carboxamido)phenyl dimethylcarbamate seed was charged into the mixture. The mixture was heated at 45-50° C. for 2-3 hours and then concentrated to about 96-108 L at batch temperature ≤50° C. under reduced pressure. Isopropanol (40 kg) was charged and the mixture was concentrated to 84-96 L batch temperature ≤50° C. under reduced pressure. This isopropanol addition/concentration process was repeated one more time with 39 kg isopropanol. The temperature of the mixture was lowered to 15-20° C. and stirred at this temperature for about 12 hours. Isopropanol (11 kg) was then added and the mixture was stirred at 15-20° C. for about 3 hours. The slurry was filtered through a centrifuge. The reactor and the wet cake in the centrifuge was washed with 28 kg of isopropanol. The product was dried at 45-50° C. under vacuum for 24 hours. The residual of N,N-diisopropylethylamine was mostly removed by stirring the product in 76 kg of water for 10-30 minutes. The product was filtered through a centrifuge and washed with 26 kg of water. The product was dried at 45-50° C. under vacuum for 24 hours to afford 12.1 kg (83% yield) 3-(4-((((benzyloxy)carbonyl)amino)methyl)-1-(5-methyl-7H-pyrrolo[2,3-d]pyrimidin-4-yl)piperidine-4-carboxamido)phenyl dimethylcarbamate with a purity of 98.8%.

3-(4-(Aminomethyl)-1-(5-methyl-7H-pyrrolo[2,3-d] pyrimidin-4-yl(piperidine-4-carboxamido)phenyl dimethylcarbamate Hydrochloride To a nitrogen inerted, 300-L stainless steel reactor at room temperature were charged 96 kg of methanol, 12 kg of 3-(4-((((benzyloxy)carbonyl(amino)methyl)-1-(5-methyl-7H-pyrrolo[2,3-d]pyrimidin-4-yl(piperidine-4-carboxamido) phenyl dimethylcarbamate, 2.3 kg of wet 10% palladium on carbon (50% water) and 8.0 kg of methanol rinse. The mixture was cooled to 0-10° C. before 17.2 kg ammonia gas was added at 0-10° C. The reactor system was vacuumed to ≤−0.06 MPa then filled with nitrogen to atmosphere. The cycle was repeated two more times with nitrogen. The reactor was then vacuumed to ≤−0.06 MPa and filled with hydrogen to 0.5 MPa. The cycle was repeated two more times. After the final cycle, the mixture was stirred at 25-30° C. for 15 hours while the pressure was maintained at 0.5-0.6 MPa by regulating the hydrogen valve and pressure release valve. The hydrogen was released and purged with nitrogen. The mixture was passed through a kieselgur pad followed by an inline polish filter and the filtrate was collected in a drum. The reactor and the filters were washed 24 kg of methanol twice. The filtrate was combined and IPC analysis showed the residual palladium was 10 ppm vs. specification of NMT 15 ppm. The filtered solution was transferred into a 500 L glass lined reactor through an inline filter. The drum and the inline filter were rinsed with 18 kg of methanol and the wash was combined with the solution. The solution was concentrated to 84-96 L at batch temperature ≤45° C. under reduced pressure. Methanol (44 kg) was charged and the solution was concentrated to 84-96 L again at batch temperature ≤45° C. under reduced pressure. Another 46 kg of methanol was added and the solution was concentrated to 108-120 L at batch temperature ≤45° C. under reduced pressure, followed by addition of 15 kg of methanol. Hydrogen chloride in ethanol (9.0 kg, prepared with 9.6 kg of absolute ethanol and 1.9 kg of acetyl chloride) was added slowly at 55-60° C. in 1.5 hours, followed by 50 kg of absolute ethanol. 3-(4-(Aminomethyl)-1-(5-methyl-7H-pyrrolo[2,3-d]pyrimidin-4-yl)piperidine-4-carboxamido)phenyl dimethylcarbamate hydrochloride seed (0.018 kg) was added. The mixture was stirred at 55-60° C. for 1-2 hours and cooled to 20-40° C. The mixture was then concentrated to 60-72 L at batch temperature ≤45° C. under reduced pressure. Anhydrous ethanol (46 kg) was added and the mixture was again concentrated to 60-72 L at batch temperature ≤45° C. under reduced pressure. The ethanol addition/concentration cycle was repeated two more times. The mixture was heated 50-60° C. and stirred for 1-2 hours, then cooled to 0-5° C. and stirred 2-3 hours. The slurry was filtered with a centrifuge and washed with 24 kg of filtered cold (−5-0° C.) anhydrous ethanol. The wet cake was charged into a 500-L glass lined reactor containing, followed by addition of 77 kg of acetonitrile. The mixture was heated to 65-70° C. and stirred for 4-5 hours, then cooled to 15-20° C. and stirred for 2-3 hours. The slurry was filtered via a centrifuge and the wet cake was washed with 24 kg of acetonitrile. The product was dried in oven at 45-50° C. for about 20 hours and de-lumped with a sieve to afford 9.01 kg (91% yield) crystalline anhydrous 3-(4-(aminomethyl)-1-(5-methyl-7H-pyrrolo[2,3-d]pyrimidin-4-yl)piperidine-4-carboxamido)phenyl dimethylcarbamate hydrochloride with a purity of 99.8%.

All references (e.g., patents and patent applications) cited above are incorporated herein by reference in their entireties.

What is claimed is:

1. A crystalline compound, which is 3-(4-(aminomethyl)-1-(5-methyl-7H-pyrrolo[2,3-d]pyrimidin-4-yl)piperidine-4-carboxamido)phenyl dimethylcarbamate or a salt thereof.

2. The crystalline compound of claim 1, which is 3-(4-(aminomethyl)-1-(5-methyl-7H-pyrrolo[2,3-d]pyrimidin-4-yl)piperidine-4-carboxamido)phenyl dimethylcarbamate freebase.

3. The crystalline compound of claim 2, which has a DSC peak at about 177.9° C.

4. The crystalline compound of claim 1, which is 3-(4-(aminomethyl)-1-(5-methyl-7H-pyrrolo[2,3-d]pyrimidin-4-yl)piperidine-4-carboxamido)phenyl dimethylcarbamate benzoate.

5. The crystalline compound of claim 4, which has a melting point of about 192.3° C. or a DSC peak at about 194.5° C.

6. The crystalline compound of claim 4, which has an XRPD spectrum comprising peaks at about 6.5, 15.6, 16.5, 18.4, 19.2, 21.3, and 24.2±0.3 degrees 2θ.

7. The crystalline compound of claim 1, which is 3-(4-(aminomethyl)-1-(5-methyl-7H-pyrrolo[2,3-d]pyrimidin-4-yl)piperidine-4-carboxamido)phenyl dimethylcarbamate hydrochloride.

8. The crystalline compound of claim 7, which has a melting point of about 245.8° C. or a DSC peak at about 248.9° C.

9. The crystalline compound of claim 7, which has an XRPD spectrum comprising peaks at about 6.4, 11.7, 17.0, 19.2, 23.0, and 25.7±0.3 degrees 2θ.

10. The crystalline compound of claim 1, which is 3-(4-(aminomethyl)-1-(5-methyl-7H-pyrrolo[2,3-d]pyrimidin-4-yl)piperidine-4-carboxamido)phenyl dimethylcarbamate phosphate.

11. The crystalline compound of claim 10, which has a melting point of about 164.6° C. or a DSC peak at about 170.9° C.

12. The crystalline compound of claim 10, which has an XRPD spectrum comprising peaks at about 4.5, 12.9, 16.0, 18.5, 20.3, 21.4, and 23.0±0.3 degrees 2θ.

13. A pharmaceutical formulation comprising the crystalline compound of claim 1 and a pharmaceutically acceptable excipient.

14. A method of preparing a crystalline salt of 3-(4-(aminomethyl)-1-(5-methyl-7H-pyrrolo[2,3-d]pyrimidin-4-yl)piperidine-4-carboxamido)phenyl dimethylcarbamate, which comprises:

heating a solution comprising 3-(4-(aminomethyl)-1-(5-methyl-7H-pyrrolo[2,3-d]pyrimidin-4-yl)piperidine-4-carboxamido)phenyl dimethylcarbamate and a pharmaceutically acceptable acid to provide a salt of 3-(4-(aminomethyl)-1-(5-methyl-7H-pyrrolo[2,3-d]pyrimidin-4-yl)piperidine-4-carboxamido)phenyl dimethylcarbamate;

reducing the solubility of the salt in the solution under conditions sufficient to provide a crystalline salt of 3-(4-(aminomethyl)-1-(5-methyl-7H-pyrrolo[2,3-d]pyrimidin-4-yl)piperidine-4-carboxamido)phenyl dimethylcarbamate; and isolating the crystalline salt.

15. A method of preparing crystalline 3-(4-(aminomethyl)-1-(5-methyl-7H-pyrrolo[2,3-d]pyrimidin-4-yl)piperidine-4-carboxamido)phenyl dimethylcarbamate hydrochloride, which comprises:

heating a solution comprising water, 3-(4-(aminomethyl)-1-(5-methyl-7H-pyrrolo[2,3-d]pyrimidin-4-yl)piperidine-4-carboxamido)phenyl dimethylcarbamate, and p-toluenesulfonic acid monohydrate;

adding an anti-solvent to the solution to provide a mixture;

cooling the mixture; and isolating crystalline 3-(4-(aminomethyl)-1-(5-methyl-7H-pyrrolo[2,3-d]pyrimidin-4-yl)piperidine-4-carboxamido)phenyl dimethylcarbamate hydrochloride from the mixture.

16. The method of claim 15, wherein the anti-solvent is acetonitrile.

17. A method of lowering intraocular pressure in a patient, which comprises administering the pharmaceutical formulation of claim 13 to the eye of a patient.

* * * * *